(12) United States Patent
Rossell

(10) Patent No.: US 6,824,751 B2
(45) Date of Patent: Nov. 30, 2004

(54) DEVICE FOR STERILIZING A CHAMBER

(75) Inventor: Jordi Rossell, Belmont-sur-Lausanne (CH)

(73) Assignee: Meditecnic Inc., Dana Point, CA (US)

( * ) Notice: Subject to any disclaimer, the term of this patent is extended or adjusted under 35 U.S.C. 154(b) by 582 days.

(21) Appl. No.: 09/921,073

(22) Filed: Aug. 2, 2001

(65) Prior Publication Data

US 2002/0018735 A1 Feb. 14, 2002

Related U.S. Application Data

(63) Continuation of application No. PCT/IB99/00188, filed on Feb. 3, 1999.

(51) Int. Cl.$^7$ ................................................. A61L 9/00
(52) U.S. Cl. ........................... 422/295; 134/1; 134/184; 422/39; 422/127; 422/292; 422/297
(58) Field of Search ............................... 422/1, 20, 39, 422/292, 295, 297, 127; 134/1, 184

(56) References Cited

U.S. PATENT DOCUMENTS

| | | | | |
|---|---|---|---|---|
| 5,305,737 A | * | 4/1994 | Vago | 601/4 |
| 5,686,045 A | * | 11/1997 | Carter | 422/20 |
| 6,696,019 B2 | * | 2/2004 | Laugharn et al. | 422/39 |

* cited by examiner

Primary Examiner—Krisanne Jastrzab
(74) Attorney, Agent, or Firm—Sturm & Fix LLP

(57) ABSTRACT

A device for cleaning and sterilizing the inside of a chamber, including a supply of sterilizing liquid for said chamber and a device for inducing variations in the pressure, amplitude, frequency and the gradient of said variations in the sterilizing liquid, whereby said device is adapted in such a way that cavitation occurs inside the liquid, the device inducing said pressure variations include a liquid column between the chamber and a switching organ, whereby the chamber can be cyclically connected to a depression, whereby the value thereof is related to the amplitude or respectively to the atmospheric pressure.

35 Claims, 2 Drawing Sheets

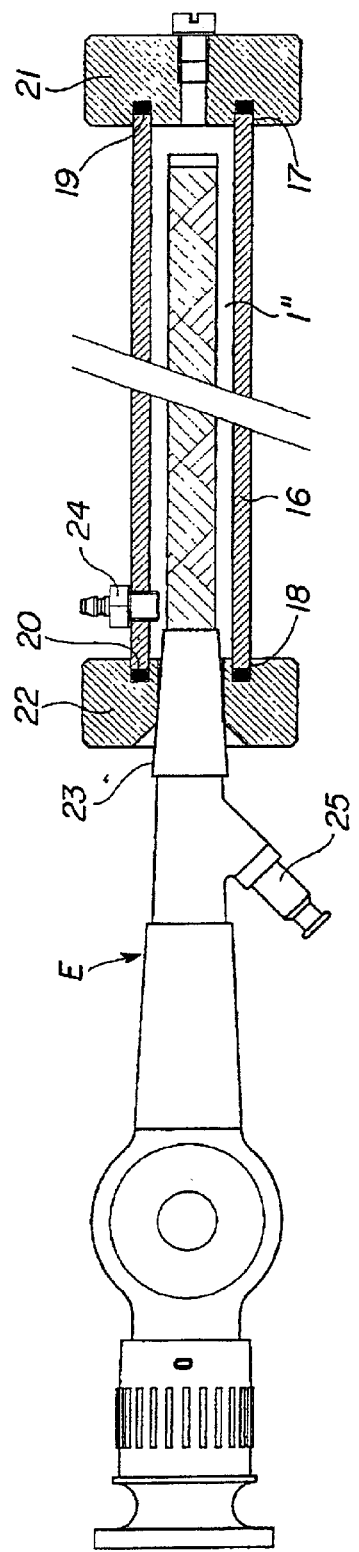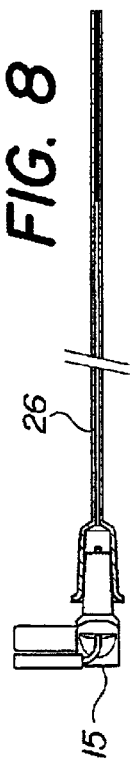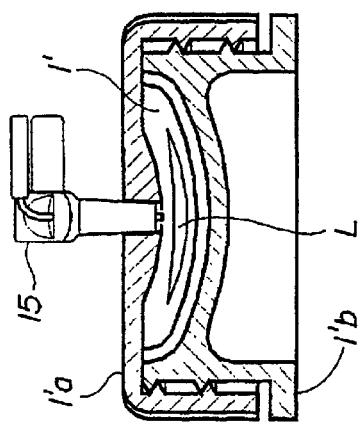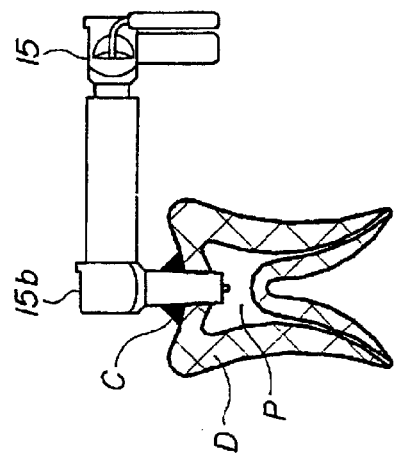

DEVICE FOR STERILIZING A CHAMBER

CROSS REFERENCE TO RELATED APPLICATIONS

This application is a Continuation application of PCT/IB99/00188 filed Feb. 3, 1999, entitled Device for Sterilizing a Chamber. Priority is claimed to the PCT application filing date under 35 U.S.C. § 365.

BACKGROUND OF THE INVENTION

1. Field of the Invention

The present invention relates to a device for cleaning and sterilizing the inside of a chamber, comprising a supply of sterilizing liquid for this chamber, and means for inducing, within this sterilizing liquid, variations in pressure, amplitude and frequency, and in the gradient of said variations, said means being adapted to generate cavitation within this liquid.

2. Description of Related Art

It has been observed that cavitation, in addition to its familiar undesirable effects in hydraulic systems, such as attack of surfaces, noise, and loss of contact with the liquid, has other characteristics which may prove beneficial in some applications.

The first of these characteristics is mechanical and makes it possible to go beyond the limits of capillarity in a cavitation regime. This property may therefore be of use when treating regions which are otherwise inaccessible.

The destructive properties can be used judiciously by exploiting the thermal wave which, although temporary, is nevertheless substantial. The same is true of the accompanying oxidation reaction. This is because the exothermal implosion of the vapor bubbles created by negative pressure on a microorganism releases its energy in a very short time and on a very small surface area, determining temporarily a very high temperature.

It is therefore the conjunction of mechanical, thermal and even chemical effects which makes it possible at one and the same time to improve the use of a cleaning and/or sterilizing agent and to increase its efficacy. The dissolution of one substance in another is thereby greatly enhanced and permits sterilization of a cavity or of a body immersed in a cavitation regime, which it would not be possible to obtain by simple rinsing or prolonged immersion with the same liquid agent.

As cavitation appears when know thermodynamic conditions in a defined liquid are satisfied, it suffices for the inside of a chamber which is closed and filled with liquid to be subjected to pressure variations which are adequate in their amplitude and form to generate cavitation in this liquid at its particular temperature. The effect of cavitation may be exerted on the liquid itself, on the walls of the container or on any body immersed therein.

The demands of the pressure signal are however very particular and are difficult to obtain solely by mechanical selection of the desired pressure levels and frequency.

The use of cavitation for cleaning and sterilizing has already been the subject of many applications in the medical field, or for cleaning and sterilizing medical or paramedical equipment. The combination of ultrasonic frequencies and of cavitation has also been proposed for cleaning and sterilizing. Reference may be made, by way of example, to DE 39 03 648 which relates to a method for inactivating viruses in a liquid by means of the cavitation generated by varying the flow speeds within the liquid. This method is implemented with the aid of a high-pressure pump and a homogenization valve placed downstream.

In EP 0,078,614, contact lenses are cleaned and disinfected in a saline solution in which cavitation is created at an ultrasonic frequency.

Another method for cleaning and sterilizing which combines ultrasound and cavitation is described in EP 0,595,783 and in U.S. Pat. No. 4,193,818. Cavitation combined with ultrasound has the disadvantage of attacking the cleaned surface.

It has also been proposed, in EP 0,299,919, to use cavitation for devitalizing teeth, an endpiece being fitted in a leaktight manner onto an opening formed to give access to the pulp chamber of the tooth. This endpiece comprises a liquid injector connected to a feed pump and a discharge conduit connected to a suction pump. The suction pump creates bubbles in the liquid, which the pressure pump causes to implode, thereby producing cavitation.

An improvement to the above device has been proposed in EP 0,521,119 in which a water-jet pump is arranged in the adjustable endpiece which can be fitted in a leaktight manner on the orifice of the pulp chamber of the tooth filled with Javel water. The inlet of this water-jet pump is connected to the outlet conduit of a piston pump, its outlet is connected to a discharge conduit, and its suction conduit opens into the pulp chamber. At each cycle of the pump, a reciprocating motion of a certain volume of liquid is produced in the discharge conduit due to the alternating compression and suction, in a conduit connecting the pump to the discharge conduit by way of a water-jet pump, generating alternating negative pressures and overpressures in the liquid of the pulp chamber, thus generating cavitation.

The first of these devices for devitalization requires two pumps and involves a high level of consumption of liquid, consisting of the treatment liquid itself. The second of these devitalization devices uses a single-action piston pump which is as it were the motor driving the water-jet pump, generating variations in pressure in the pulp chamber. The piston pump used for this purpose produces a sinusoidal pressure which, starting from the closure of a single-action valve, increases until it reaches the gradient of the sinusoid. Only the gradient is useful in creating cavitation, and this gradient must be as steep as possible in order to create a variation which is as sudden as possible. Given that the sinusoidal variation does not suffice by itself to cause the desired cavitation, it acts on the pressure of the pulp chamber by way of a body of liquid which it causes to move and works as a resonator to create the required sudden pressure variations by way of the water-jet pump.

BRIEF SUMMARY OF THE INVENTION

It is an object of the present invention to attain required sudden pressure variations, but directly without the aid of a water-jet pump, that is to say without a positive pressure generator. To this end, the subject of the present invention is a device for cleaning and sterilizing the inside of a chamber. By using a switching member it is possible for a column of liquid, connecting this switching member to the sterilization chamber, to be brought into communication with two defined pressure levels, the difference between these corresponding to the desired amplitude, so that the gradient of the variation is very considerable, and only the losses of head in the conduits influence this gradient since the pressures of the two levels are constant. In addition, the pressure of just one of the two pressure levels must be created artificially, while that of the other level, corresponding to the highest pressure, is simply the atmospheric pressure. The system therefore functions as a spring piston which tends constantly to be brought back to one of its two positions by the return spring. In the case of the present invention, the spring is formed by the atmospheric pressure.

BRIEF DESCRIPTION OF THE DRAWINGS

The attached drawings illustrate diagrammatically and by way of example an embodiment of the cleaning and sterilizing device which forms the subject of the present invention.

FIG. 5 is a view showing the detail from FIG. 3 mounted on a tooth shown in cross section, in accordance with the first use;

FIG. 6 is a view showing the detail from FIG. 3 mounted on a cleaning and sterilizing chamber for contact lenses;

FIG. 7 is an elevation view of an endoscope, part of which is lodged in a sterilizing chamber of the device according to the invention, specifically adapted for this use; and FIG. 8 is an elevation view, partially in cross section, of another application of the invention.

DETAILED DESCRIPTION OF THE INVENTION

Figure 1:
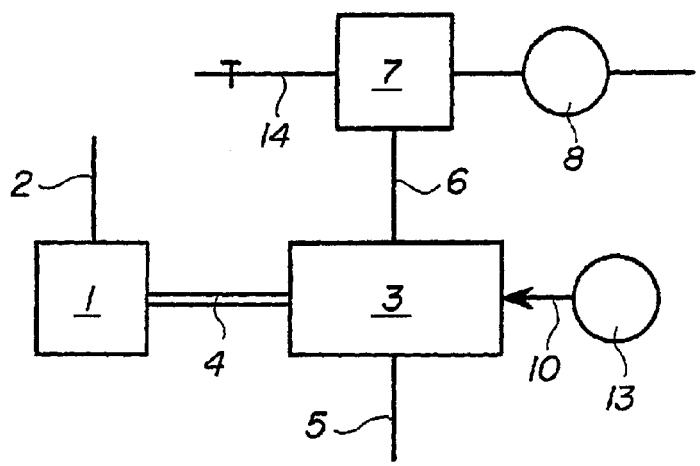
FIG. 1 is a block diagram showing the principle of the device.

The cleaning device whose operating principle is illustrated by FIG. 1 comprises a treatment chamber 1 connected on the one hand to a calibrated supply of treatment liquid 2 and on the other hand to a distribution or switching member 3 by way of a conduit 4. A first inlet 5 of this switching member 3 communicates with the atmospheric pressure and a second inlet 6 communicates with a low pressure source 7 connected to a vacuum pump 8, and to an adjustable auxiliary air inlet 14. This switching member 3, which is represented in more detail in FIG. 2, comprises a cylindrical body through which there runs an axial channel into which the conduits 5 and 6 open laterally, and of which one axial end communicates with the conduit 4 connecting this switching member to the treatment chamber 1.

A distribution rotor 10 is mounted in this axial channel, and an O-ring seal 11 fitted around the rotor at one end of the block 9 and held in place by a lid 12 ensures the leaktightness of the axial channel. The end of the distribution rotor 10 protruding from the block 9 is integral with the drive shaft of a motor 13. The end of the rotor 10 communicating with the conduit 4 has an axial passage 10a provided with two slots 10b and 10c which are intended to bring the axial passage 10a cyclically into communication with the conduit 5 and the atmospheric pressure and, respectively, with the conduit 6 and the vacuum source.

Figure 2:
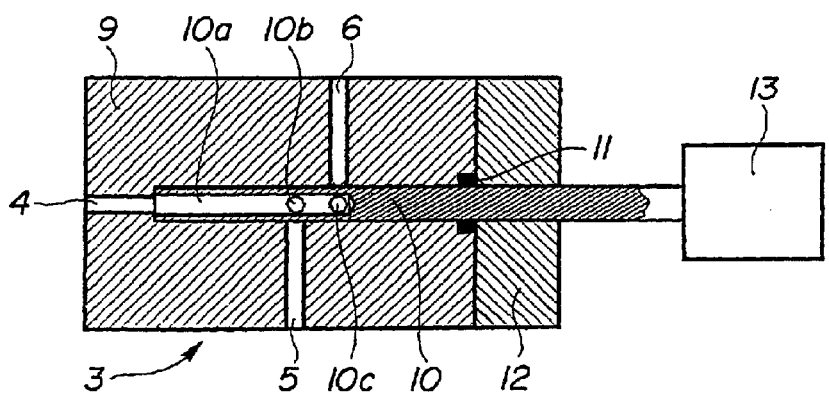
FIG. 2 is a cross-sectional view of a detail from FIG. 1.

The first phase of the cyclical process generated by the device which has just been described involves suddenly lowering the pressure in the treatment chamber 1 to below the vapor pressure of the treatment liquid which fills this chamber 1, bringing it into communication with the low pressure source 7, the rotor 10 then being located in the angular position illustrated in FIG. 2. The temperature, the nature of the liquid and its purity will have an influence on the level and the gradient of the necessary variation. Each impurity or mechanical discontinuity will be a potential bubble interference for a given liquid. It should be noted that in the case of the present invention, this gradient is very steep, and only the losses of head via the conduits come into consideration for establishing the negative pressure in the chamber 1, by contrast there is no longer the interference of the sinusoidal movement of a pump, as in the solutions of the prior art.

The second phase of this process consists in causing implosion of the vapor bubbles created in the first phase, by re-establishing the atmospheric pressure in the chamber 1, which is obtained by the rotation of the rotor 10 which brings the slot 10b into communication with the conduit 5 and the atmospheric pressure. The liquid which had been suctioned in the conduit 4 then returns to the chamber, creating a slight instantaneous overpressure which triggers simultaneous implosion of all the vapor bubbles previously formed.

The maximum effect of the change of state is proportional to the vacuum maintained in the low pressure source 7 by a diaphragm pump 8. The vacuum level can however be modulated as a function of the desired power by virtue of the adjustable auxiliary air inlet 14.

The system is filled, by way of the treatment chamber 1, with the supply of calibrated liquid 2, the mean pressure being negative in the operating mode. The reciprocating action of the liquid column is in fact provided only for a correctly primed conduit and regeneration of the liquid is desirable even if it opens the system.

The speed of rotation of the motor 13 driving the rotor 10 is adjustable as a function of the nature of the liquid used, its temperature and the chosen negative pressure. The state of the mixture removed from the treatment chamber 1 (proportion of dissolved gas) through the conduit 4 plays a role and may require adaptation, in particular during the operation of dissolution.

The dimensions and the rigidity of the conduit 4 connecting the treatment chamber 1 to the switching member 3 are in relation to the frequency of the cycle. A conduit made of polyurethane and with an internal diameter of 2 mm and a 1-mm wall and length of 320 mm has given good results at a frequency of the order of 15 to 25 Hz with most of the liquids used. This size is suitable for generating a good cavitation regime in volumes of up to several $cm^3$. The dimensions of the restriction of the inlet for fresh liquid entail a compromise between good filling of the tubing and the inherent loss of vacuum; a tube made of stainless steel with an internal diameter of 0.3 mm and a length of 15 mm has given good results. The operational output depends on the liquid used and is of the order of 10 m/min.

The calibration of the air inlet 14 depends on the diaphragm pump used. A regulating valve offers the best ease of use. The diaphragm pump must be such as to make it possible to reach, in the low pressure source 7, a vacuum of at least $-0.9.10^5$ Pa in the operating regime when the air inlet 14 is completely closed. It should be noted that this pressure is in itself higher than the vapor pressure of the liquid. However, by virtue of the liquid column 4, it is possible in a dynamic regime to reach peaks lower than the value of the negative pressure in the low pressure source 7.

Figure 3:
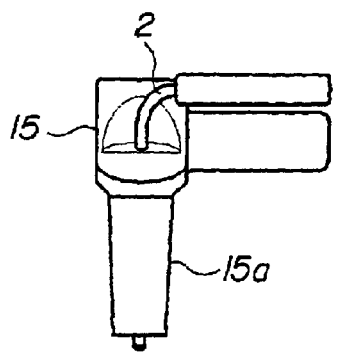
FIG. 3 is an elevation view of another detail from FIG. 1.
Figure 4:
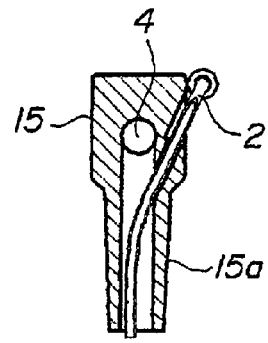
FIG. 4 is a view along IV—IV in FIG. 3.

FIGS. 3 to 5 illustrate an application of the device which has just been described, in which it is used for devitalizing a tooth. In this particular use, the treatment chamber 1 is formed by the pulp chamber P of the tooth D to be devitalized, an endpiece 15 being intended to connect the pulp chamber P of the tooth D on the one hand to the supply 2 of treatment liquid and on the other hand to the conduit 4 connecting the pulp chamber P to the switching member 3.

As is shown in FIG. 5, the endpiece 15 comprises a joining element 15a fitted in a leaktight manner in a flexible connection element 15b which itself is fitted in an opening formed in the tooth D to permit access to the pulp chamber P of the tooth D. A seal of cement C formed around the flexible connection element 15b serves to ensure the leaktightness of the treatment chamber. This use offers a real advantage in pulpectomy of vital or nonvital roots. The action of the sodium hypochlorite traditionally used is rendered more effective by an increased interface between the corrosive liquid and the tooth nerve, reaching into the very smallest nooks and corners, which are even inaccessible manually. The sterilizing effect of the cavitation adds to the efficacy of the intervention, eliminating any residual microorganisms. Moreover, the operation is noninvasive, thereby reducing the trauma inflicted.

The use of the supplementary connection element offers a connection which is more ergonomic and which is advantageously flexible. It also has the advantage of allowing the endpiece 15 to be removed and put back in place without having to break the cement C.

FIG. 6 illustrates another advantageous use of the present invention for wetting and sterilizing soft contact lenses. It will be seen in this figure that an endpiece 15 is fixed in an opening giving access to the inside of a treatment chamber 1' in which a soft contact lens L is immersed. The treatment chamber 1' is made up of two parts 1a', 1b' which are joined to each other in a leaktight manner, for example by a bayonet-type catch. This hydrophilic contact lens can be freed of all microorganisms by creating cavitation of the volume of liquid in which it is wetted for a duration of the order of 10 min. Immersion, even for the whole night, in the same specific disinfecting product does not by itself achieve the bacterial decontamination deriving from this use.

FIG. 7 illustrates a further advantageous use of the device according to the invention, for endoscopy devices which are not autoclaved, and in particular those which are provided with a channel for biopsy forceps. Such devices are in fact never rendered sterile by simple immersion in the disinfecting liquid to which they are subjected after each use. The cavitation and the circulation of the disinfecting agent in which they are plunged sterilizes them effectively and allows them to be reused after a short time.

The treatment chamber 1" in which the active end of the endoscope E is fitted comprises a tube 16 whose ends are engaged in two annular grooves 17, 18, respectively, at the bottom of which there are O-ring seals 19, 20, respectively. The annular groove 17 is formed in a closure member 21, while the groove 18 is formed in a closure ring 22 intended to engage against a frustoconical part 23 of the endoscope E. A joining piece 24 passes through the wall of the tube 16 and is used to connect the inside of the tube to the cavitation generator in FIG. 1. The inside of the tube 16 which serves as a treatment chamber is fed with treatment liquid via the access channel 25 for the biopsy forceps of the endoscope, when such a channel exists. Otherwise, it can be supplied directly through the wall of the tube 16.

Another use very similar to that described in FIG. 6 could be applied to the unblocking of catheters. which could be done without removing the catheter. For this purpose, as is illustrated in FIG. 8, the endpiece 15 is fixed to the end of the catheter 26 intended for perfusion. Cavitation will occur as long as the clot blocks the passage, inducing an anticoagulating liquid as far as the interface of the blood clot obstructing the conduit of the catheter 26. Cavitation will stop spontaneously upon reappearance of a flow of fresh blood being drawn in, evidence of a successful operation, after which perfusion can be reinstated in place of the endpiece 15.

The use of the device described could also extend to the unblocking of arterial or venous conduits. However, in this case, and given the fact that the walls of these conduits are not rigid, means would be needed to prevent crushing of these conduits, given that in order to create cavitation the pressure has to drop to below the atmospheric pressure.

Of course, the dimensions of the vacuum source 7 and of the switching member will need to be adapted to the volume necessary for the treatment chamber.

Applications other than those previously described, and using the same cleaning and sterilizing device, are of course available.

What is claimed is:

1. Apparatus for cleaning and sterilizing the inside of a treatment chamber, comprising:

a supply of sterilizing liquid for this treatment chamber; and, means for inducing, within this sterilizing liquid, variations in pressure, amplitude and frequency, and slope of said variations, said means being adapted to generate cavitation within this liquid and comprising a liquid column arranged between said treatment chamber and a switching member with which the treatment chamber can be connected in a cyclic way to a negative pressure, the value of the latter being in relation to said amplitude or respectively to the atmospheric pressure, wherein a main conduit connects said switching member to said treatment chamber, two conduits connect said main conduit to the atmospheric pressure and to said negative pressure, respectively, said switching member comprising connecting passages between said conduits and said main conduit and being movable between at least two positions, one in which one of said connecting passages brings the main conduit into communication with the atmosphere, the other in which the other of said passages brings the main conduit into communication with said negative pressure, and drive means for displacing said switching member from one position to the other and vice versa.

2. Apparatus according to claim 1, wherein said switching member is a rotary member and is integral in kinematic terms with the output shaft of a drive motor.

3. Apparatus according to claim 1, further comprising:

an endpiece intended to connect said treatment chamber on the one hand to said switching member and on the other hand to said supply of sterilizing liquid.

4. Apparatus according to claim 3, wherein a second flexible connection element connected in a leaktight and removable manner to said endpiece is arranged between said switching member and said treatment chamber.

5. Apparatus according claim 1, wherein said treatment chamber is made up of two parts which are joined to each other in a removable and leaktight manner.

6. Apparatus according to one of claim 1, wherein said treatment chamber is made up of a tubular element, one end of which is open to receive the working part of an endoscope, the inside of said treatment chamber being connected on the one hand to said switching member by way of a joining piece and to said supply of sterilizing liquid via the inlet channel for the biopsy forceps of said endoscope.

7. Apparatus according to claim 6, wherein said treatment chamber includes a tubular element which is open at both its ends, each of said ends being sealingly engaged in a respective annular groove in two respective closure members, with interposition of a sealing joint.

8. Apparatus according to claim 1, further comprising:
an endpiece intended to connect said treatment chamber on the one hand to said switching member and on the other hand to said supply of sterilizing liquid.

9. Apparatus according to claim 2, further comprising:
an endpiece intended to connect said treatment chamber on the one hand to said switching member and on the other hand to said supply of sterilizing liquid.

10. Apparatus according to claim 8, wherein a second flexible connection element connected in a leaktight and removable manner to said endpiece is arranged between said switching member and said treatment chamber.

11. Apparatus according to claim 9, wherein a second flexible connection element connected in a leaktight and removable manner to said endpiece is arranged between said switching member and said treatment chamber.

12. Apparatus according claim 1, wherein said treatment chamber is made up of two parts which are joined to each other in a removable and leaktight manner.

13. Apparatus according claim 2, wherein said treatment chamber is made up of two parts which are joined to each other in a removable and leaktight manner.

14. Apparatus according claim 3, wherein said treatment chamber is made up of two parts which are joined to each other in a removable and leaktight manner.

15. Apparatus according claim 4, wherein said treatment chamber is made up of two parts which are joined to each other in a removable and leaktight manner.

16. Apparatus according claim 8, wherein said treatment chamber is made up of two parts which are joined to each other in a removable and leaktight manner.

17. Apparatus according claim 9, wherein said treatment chamber is made up of two parts which are joined to each other in a removable and leaktight manner.

18. Apparatus according to claim 1, wherein said treatment chamber is made up of a tubular element, one end of which is open to receive the working part of an endoscope, the inside of said treatment chamber being connected on the one hand to said switching member by way of a joining piece and to said supply of sterilizing liquid via the inlet channel for the biopsy forceps of said endoscope.

19. Apparatus according to claim 2, wherein said treatment chamber is made up of a tubular element, one end of which is open to receive the working part of an endoscope, the inside of said treatment chamber being connected on the one hand to said switching member by way of a joining piece and to said supply of sterilizing liquid via the inlet channel for the biopsy forceps of said endoscope.

20. Apparatus according to claim 3, wherein said treatment chamber is made up of a tubular element, one end of which is open to receive the working part of an endoscope, the inside of said treatment chamber being connected on the one hand to said switching member by way of a joining piece and to said supply of sterilizing liquid via the inlet channel for the biopsy forceps of said endoscope.

21. Apparatus according to claim 4, wherein said treatment chamber is made up of a tubular element, one end of which is open to receive the working part of an endoscope, the inside of said treatment chamber being connected on the one hand to said switching member by way of a joining piece and to said supply of sterilizing liquid via the inlet channel for the biopsy forceps of said endoscope.

22. Apparatus according to claim 9, wherein said treatment chamber is made up of a tubular element, one end of which is open to receive the working part of an endoscope, the inside of said treatment chamber being connected on the one hand to said switching member by way of a joining piece and to said supply of sterilizing liquid via the inlet channel for the biopsy forceps of said endoscope.

23. Apparatus according to claim 18, wherein said treatment chamber includes a tubular element which is open at both its ends, each of said ends being sealingly engaged in a respective annular groove in two respective closure members, with interposition of a sealing joint.

24. Apparatus according to claim 19, wherein said treatment chamber includes a tubular element which is open at both its ends, each of said ends being sealingly engaged in a respective annular groove in two respective closure members, with interposition of a sealing joint.

25. Apparatus according to claim 20, wherein said treatment chamber includes a tubular element which is open at both its ends, each of said ends being sealingly engaged in a respective annular groove in two respective closure members, with interposition of a sealing joint.

26. Apparatus according to claim 21, wherein said treatment chamber includes a tubular element which is open at both its ends, each of said ends being sealingly engaged in a respective annular groove in two respective closure members, with interposition of a sealing joint.

27. Apparatus according to claim 22, wherein said treatment chamber includes a tubular element which is open at both its ends, each of said ends being sealingly engaged in a respective annular groove in two respective closure members, with interposition of a sealing joint.

28. Apparatus for cleaning and sterilizing the inside of a treatment chamber, comprising:
a supply of sterilizing liquid for this treatment chamber;
means for inducing, within this sterilizing liquid, variations in pressure, amplitude and frequency, and slope of said variations, said means being adapted to generate cavitation within this liquid, and comprising a liquid column arranged between said treatment chamber and a switching member with which the treatment chamber can be connected in a cyclic way to a negative pressure, the value of the latter being in relation to said amplitude or respectively to the atmospheric pressure; and
an endpiece intended to connect said treatment chamber on the one hand to said switching member and on the other hand to said supply of sterilizing liquid.

29. Apparatus according to claim 28 wherein a second flexible connection element connected in a leaktight and removable manner to said endpiece is arranged between said switching member and said treatment chamber.

30. Apparatus according claim 28, wherein said treatment chamber is made up of two parts which are joined to each other in a removable and leaktight manner.

31. Apparatus according claim 29, wherein said treatment chamber is made up of two parts which are joined to each other in a removable and leaktight manner.

32. Apparatus according to claim 28, wherein said treatment chamber is made up of a tubular element, one end of which is open to receive the working part of an endoscope, the inside of said treatment chamber being connected on the one hand to said switching member by way of a joining piece and to said supply of sterilizing liquid via the inlet channel for the biopsy forceps of said endoscope.

33. Apparatus according to claim 29, wherein said treatment chamber is made up of a tubular element, one end of which is open to receive the working part of an endoscope, the inside of said treatment chamber being connected on the one hand to said switching member by way of a joining piece and to said supply of sterilizing liquid via the inlet channel for the biopsy forceps of said endoscope.

34. Apparatus for cleaning and sterilizing the inside of a treatment chamber, comprising:

a supply of sterilizing liquid for this treatment chamber; and, means for inducing, within this sterilizing liquid, variations in pressure, amplitude and frequency, and slope of said variations, said means being adapted to generate cavitation within this liquid and comprising a liquid column arranged between said treatment chamber and a switching member with which the treatment chamber can be connected in a cyclic way to a negative pressure, the value of the latter being in relation to said amplitude or respectively to the atmospheric pressure, wherein said treatment chamber is made up of a tubular element, one end of which is open to receive the working part of an endoscope, the inside of said treatment chamber being connected on the one hand to said switching member by way of a joining piece and to said supply of sterilizing liquid via the inlet channel for the biopsy forceps of said endoscope.

35. Apparatus according to claim 34, wherein said treatment chamber includes a tubular element which is open at both its ends, each of said ends being sealingly engaged in a respective annular groove in two respective closure members, with interposition of a sealing joint.

* * * * *